US012312358B2

(12) United States Patent
Yang et al.

(10) Patent No.: US 12,312,358 B2
(45) Date of Patent: May 27, 2025

(54) CRYSTALLINE PYRIMIDINYL-3,8-DIAZABICYCLO[3.2.1]OCTANYLMETHANONE COMPOUND AND USE THEREOF (71) Applicant: Pfizer Inc., New York, NY (US)

(72) Inventors: Xiaojing Yang, Waterford, CT (US); Amanda Patrice Surajhie Samuel, Somerville, MA (US)

(73) Assignee: PFIZER INC., New York, NY (US)

( * ) Notice: Subject to any disclaimer, the term of this patent is extended or adjusted under 35 U.S.C. 154(b) by 955 days.

(21) Appl. No.: 17/430,373

(22) PCT Filed: Feb. 12, 2020

(86) PCT No.: PCT/IB2020/051128
§ 371 (c)(1),
(2) Date: Aug. 12, 2021

(87) PCT Pub. No.: WO2020/165788
PCT Pub. Date: Aug. 20, 2020

(65) Prior Publication Data
US 2022/0144846 A1 May 12, 2022

Related U.S. Application Data (60) Provisional application No. 62/806,180, filed on Feb. 15, 2019.

(51) Int. Cl.
*C07D 487/08* (2006.01)
*A61K 31/506* (2006.01)
*A61P 17/00* (2006.01)
*A61P 19/02* (2006.01)
*A61P 37/00* (2006.01)

(52) U.S. Cl.
CPC .......... *C07D 487/08* (2013.01); *A61K 31/506* (2013.01); *A61P 17/00* (2018.01); *A61P 19/02* (2018.01); *A61P 37/00* (2018.01); *C07B 2200/13* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 5,023,556 | A | 5/1991 | Woodle et al. |
| 9,035,074 | B2 | 5/2015 | Brown et al. |
| 9,663,526 | B2 | 5/2017 | Fensome et al. |
| 2016/0052930 | A1* | 2/2016 | Fensome .............. A61P 17/16 514/249 |

FOREIGN PATENT DOCUMENTS

| | | |
|---|---|---|
| CN | 107074867 A | 8/2017 |
| JP | 2017-524022 A | 8/2017 |
| WO | 2016/027195 A1 | 2/2016 |

OTHER PUBLICATIONS

Merriam-Webster. (n.d.). Substantial. In Merriam-Webster.com dictionary. Retrieved Aug. 19, 2024, from https://www.merriam-webster.com/dictionary/substantial (Year: 2024).*
Healy et. al. ((2017), Pharmaceutical solvates, hydrates, and amorphous forms: A special emphasis on cocrystals, Advanced Drug Delivery Reviews, 117, 25-46 (Year: 2017).*
Russian Office Action for corresponding Russian application No. 2021123925, 37 pages, dated Apr. 14, 2022.
Russian Search Report for corresponding Russian application No. 2021123925 37 pages, dated Apr. 14, 2022.
Caira: "Crystalline Polymorphism of Organic Compounds", Topics in Current Chemistry vol. 198, pp. 163-208, 1998, Springer-Verlag.
Morissette et al.: "High-throughput Crystallization: Polymorphs, Salts, Co-crystals and Solvates of Pharmaceutical Solids", Advanced Drug Delivery Reviews, vol. 56, pp. 275-300 2004, Elsevier Science.
Bernstein "Polymorphism in Molecular Crystals" Moscow: Nauka, 2007, Chapter 7.3.2: Biodostupnost (Bioavailability), pp. 324-330.
Indian Office Action for corresponding Indian application No. 202117036455, 7 pages, dated Dec. 9, 2021.
Japanese Office Action for corresponding Japanese application No. 2020-021119, 12 pages, dated Oct. 4, 2021.
Hirayama, Noriaki (Ed.), Yukikagobutsu Kessho Sakusei Handbook—Genri to Know-how (Crystal Preparation Handbook for Organic Compounds—Principle and Know-how), 2008, pp. 17-23, 37-40, 45-51, 57-65.
Kawaguchi, Yoko et al., Drug and Crystal Polymorphism, Journal of Human Environmental Engineering, 2002, vol. 4, No. 2, pp. 310-317.
Japanese Examiner'sReport for corresponding Japanese application No. 2020-021119; 6 pages, dated Dec. 19, 2022.
Australian Examination Report for corresponding Australian application No. 2020222083, 3 pages, dated Feb. 2, 2022.
Japanese Office Action for corresponding Japanese application No. 2018-021119; 6 pages, dated Jun. 20, 2022.
Moribe Kunikaze et al., "Preparation and Evaluation of Non-crystalline medicaments", Cryobiology and Cryotechnology, vol. 51, No. 1, 19-24, 2005; Japanese Society for Cryobilogy and Cryotechnology; Tsukuba, Japan.

(Continued)

*Primary Examiner* — Juliet C Switzer
*Assistant Examiner* — Dawanna Shar-Day White
(74) *Attorney, Agent, or Firm* — Casimir Jones SC; Lisa Mueller; Tristan A. Fuierer (57) ABSTRACT

The present invention discloses a novel crystalline form of ((S)-2,2-difluorocyclopropyl)-((1R,5S)-3-(2-((1-methyl-1H-pyrazol-4-yl)amino)-pyrimidin-4-yl)-3,8-diazabicyclo[3.2.1]octan-8-yl)methanone free base, pharmaceutical composition containing the same, preparations thereof and uses thereof.

17 Claims, 4 Drawing Sheets

(56) References Cited

OTHER PUBLICATIONS

Fensome et al, "Dual Inhibition of TYK2 and JAK1 for the Treatment of Autoimmune Diseases: Discovery of ((S)-2,2-Difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone (PF-06700841)", Journal of Medicinal Chemistry 61:8597-8612 (2018).

Wrobleski et al., "Highly Selective Inhibition of Tyrosine Kinase 2 (TYK2) for the Treatment of Autoimmune Diseases: Discovery of the Allosteric Inhibitor BMS-986165", Journal of Medicinal Chemistry 62:8973-8995 (2019).

PCT International Search Report and Written Opinion for International Application No. PCT/IB2020/051128 issued on May 8, 2020.

Canadian Office Action for corresponding Canadian patent application No. 3, 130,034, 4 pages, dated Oct. 4, 2022.

European Office Action for corresponding European Patent Application No. 20 708 183.7, 5 pages, dated Aug. 2, 2022.

Singapore Search Report and Written Opinion for corresponding Singapore patent application No. 11202108863W, 9 bages, dated Nov. 15, 2022.

Russian Office Action for corresponding Russian patent application No. 2021123925, 12 pages, dated Oct. 12, 2022.

Rodriguez-Spong et al. "General principles of pharmaceutical solid polymorphism: A supramolecular perspective", Advanced Drug Delivery Reviews, vol. 56, Issue 3, pp. 241-274; Feb. 23, 2004, Elsevier.

* cited by examiner

CRYSTALLINE PYRIMIDINYL-3,8-DIAZABICYCLO[3.2.1] OCTANYLMETHANONE COMPOUND AND USE THEREOF

This application is a continuation of PCT International Application No. PCT/IB2020/051128, having an International Filing Date of 12 Feb. 2020, which claims the benefit under 35 U.S.C. § 119 (e) of Ser. No. 62/806,180, filed Feb. 15, 2019.

FIELD OF THE INVENTION

The present invention relates to a crystalline form of ((S)-2,2-difluorocyclopropyl)-((1R,5S)-3-(2-((1-methyl-1H-pyrazol-4-yl)amino)pyrimidin-4-yl)-3,8-diazabicyclo [3.2.1]-octan-8-yl)methanone. The present invention also relates to pharmaceutical compositions comprising a crystalline form, and to methods for preparing such forms. The invention further relates to the use of a crystalline form in the treatment of various diseases and methods of preparation thereof.

BACKGROUND OF THE INVENTION ((S)-2,2-Difluorocyclopropyl)-((1R,5S)-3-(2-((1-methyl-1H-pyrazol-4-yl)amino)-pyrimidin-4-yl)-3,8-diazabicyclo [3.2.1]octan-8-yl)methanone has the chemical formula $C_{18}H_{21}F_2N_7O$ and the following structural formula:

The synthesis of ((S)-2,2-difluorocyclopropyl)-((1R,5S)-3-(2-((1-methyl-1H-pyrazol-4-yl)amino)-pyrimidin-4-yl)-3,8-diazabicyclo[3.2.1]octan-8-yl)methanone is described in commonly assigned U.S. Pat. No. 9,663,526, the contents of which are incorporated herein by reference in its entirety. The crystalline form of ((S)-2,2-difluorocyclopropyl)-((1R,5S)-3-(2-((1-methyl-1H-pyrazol-4-yl)amino)-pyrimidin-4-yl)-3,8-diazabicyclo[3.2.1]-octan-8-yl)methanone free base, is useful as an inhibitor of protein kinases, such as the enzyme Janus Kinase (JAK) and as such is useful therapeutically as an immunosuppressive agent for organ transplants, xenotransplantation, lupus, multiple sclerosis, rheumatoid arthritis, psoriatic arthritis, inflammatory bowel disease (IBD), psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable. The present invention relates to a novel solid form of the free base form that possesses improved material properties for use in the manufacture of a pharmaceutical dosage form.

Based on a chemical structure, one cannot predict with any degree of certainty whether a compound will crystallize, under what conditions it will crystallize, how many crystalline solid forms of the compound might exist, or the solid-state structure of any of those forms. A key characteristic of any crystalline drug is the polymorphic behavior of such a material. In general, crystalline forms of drugs are preferred over noncrystalline forms of drugs and drug intermediates, in part, because of their superior stability. For example, in many situations, a noncrystalline drug is observed to convert to a crystalline drug form upon storage. Because noncrystalline and crystalline forms of a drug typically have differing physical properties and chemical properties, such interconversion may be undesirable for safety reasons in pharmaceutical usage. The different physical properties exhibited by different solid forms of a pharmaceutical compound can affect important pharmaceutical parameters such as storage, stability, compressibility, density (important in formulation and product manufacturing), and dissolution rates (important in determining bioavailability). Stability differences may result from changes in chemical reactivity (e.g., differential hydrolysis or oxidation, such that a dosage form comprising a certain polymorph can discolor more rapidly than a dosage form comprising a different polymorph), mechanical changes (e.g., tablets can crumble on storage as a kinetically favored crystalline form converts to thermodynamically more stable crystalline form), or both (e.g., tablets of one polymorph can be more susceptible to breakdown at high humidity).

Solubility differences between polymorphs may, in extreme situations, result in transitions to crystalline forms that lack potency or result in overexposure. In addition, the physical properties of a crystalline form may also be important in pharmaceutical processing. For example, a particular crystalline form may form solvates more readily or may be more difficult to filter and wash free of impurities than other crystalline forms (i.e., particle shape and size distribution might be different between one crystalline form relative to other forms).

There is no one ideal physical form of a drug because different physical forms provide different advantages. The search for the most stable form is arduous and the outcome is unpredictable. Thus it is important to seek a variety of unique drug forms, e.g., salts, polymorphs, non-crystalline forms, which may be used in various formulations. The selection of a drug form for a specific formulation or therapeutic application requires consideration of a variety of properties, and the best form for a particular application may be one which has one specific important good property while other properties may be acceptable or marginally acceptable.

The successful development of a drug requires that it meet certain general requirements to be a therapeutically effective treatment for patients. These requirements fall into two categories: (1) requirements for successful manufacture of dosage forms, and (2) requirements for successful drug delivery and disposition after the drug formulation has been administered to the patient.

Different crystalline solid forms of the same compound often possess different solid-state properties such as melting point, solubility, dissolution rate, hygroscopicity, powder flow, mechanical properties, chemical stability and physical stability. These solid-state properties may offer advantages in filtration, drying, and dosage form manufacturing unit operations. Thus, once different crystalline solid forms of the same compound have been identified, the optimum crystalline solid form under any given set of processing and manufacturing conditions may be determined as well as the different solid-state properties of each crystalline solid form.

Polymorphs of a molecule can be obtained by a number of methods known in the art. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, solid state nuclear magnetic resonance (NMR), infrared (IR) spectroscopy, Raman spectroscopy, and hot-stage optical microscopy.

The present invention is directed to a crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone free base. The invention is also directed to compositions, including pharmaceutical compositions, containing crystalline ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone free base. The invention is further directed to processes for preparing crystalline ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone free base.

Because drug formulations, showing, for example, enhanced bioavailability or stability are consistently sought, there is an ongoing need for new or purer polymorphic forms of drug molecules. The polymorph of ((S)-2,2-difluorocyclopropyl)((1R,5S)-3-(2-((1-methyl-1H-pyrazol-4-yl)amino)-pyrimidin-4-yl)-3,8-diazabicyclo[3.2.1]octan-8-yl)methanone described herein helps meet these and other needs.

SUMMARY OF THE INVENTION

The present invention provides a crystalline form of ((S)-2,2-difluorocyclopropyl)-((1R,5S)-3-(2-((1-methyl-1H-pyrazol-4-yl)amino)-pyrimidin-4-yl)-3,8-diazabicyclo[3.2.1]-octan-8-yl)methanone.

Figure 1:
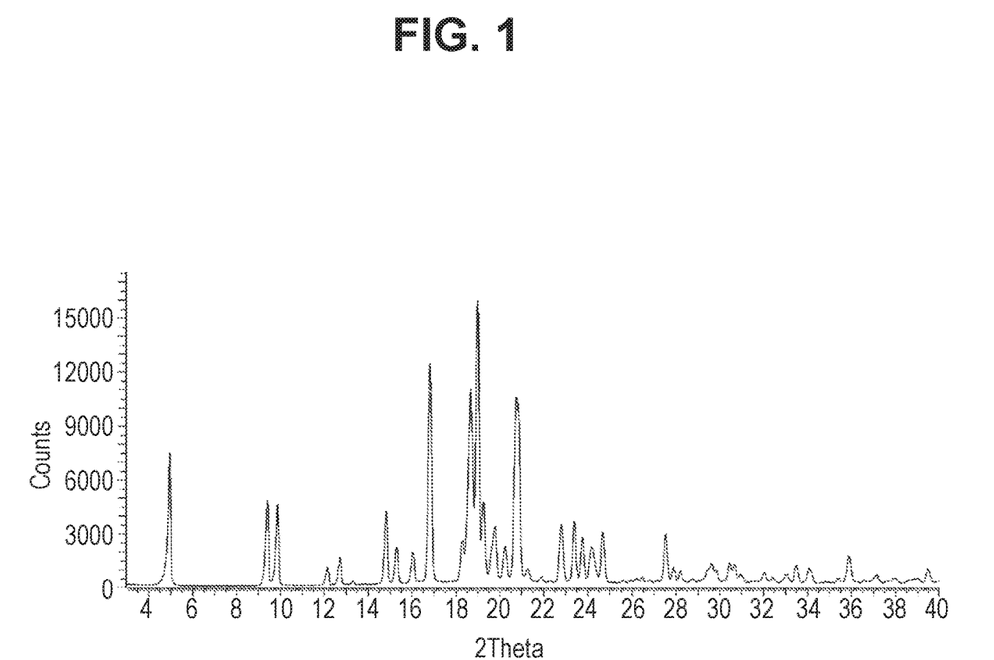
FIG. 1 depicts a powder X-ray diffraction pattern of the crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone.
Figure 2:
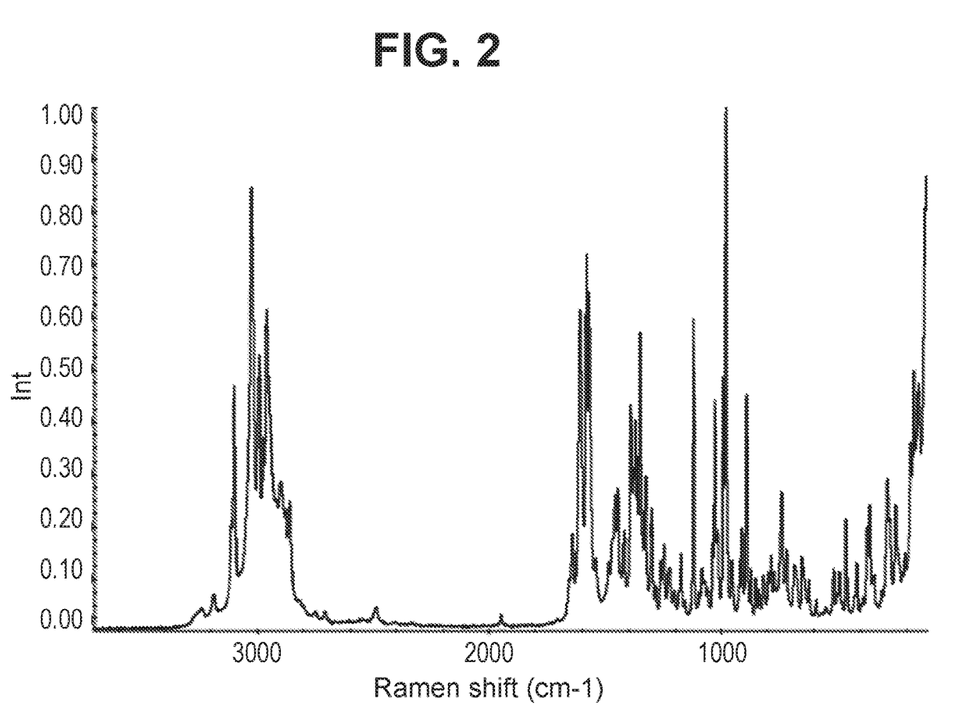
FIG. 2 depicts a Raman spectrum of the crystalline form of ((S)-2,2-difluorocyclopropyl)((1R,5S)-3-(2-((1-methyl-1H-pyrazol-4-yl)amino)-pyrimidin-4-yl)-3,8-diazabicyclo[3.2.1]octan-8-yl)methanone.
Figure 3:
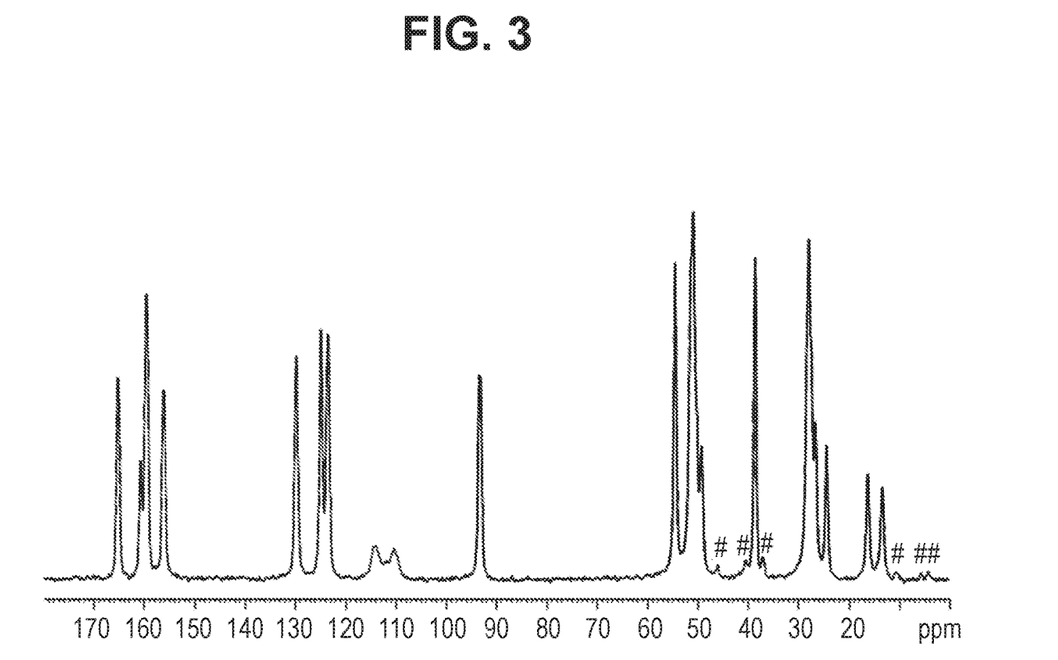
FIG. 3 depicts a solid state $^{13}$C nuclear magnetic resonance spectrum of the crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone. Spinning sidebands are noted with hash marks.

In one aspect, the present invention comprises a crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone having one or more characteristics selected from the group consisting of:
  I) a powder X-ray powder diffraction pattern comprising:
    (a) one, two, three, four, five, or more than five peaks selected from the group consisting of the peaks in Table 1 in °2θ±0.2 °2θ; (b) one, two, three, four, five, or more than five peaks selected from the group consisting of the characteristic peaks in Table 1 in °2θ±0.2 °2θ; or, (c) peaks at 2θ values essentially the same as shown in FIG. 1;
  II) a Raman spectrum comprising: (a) one, two, three, four, five, or more than five wavenumber (cm−1) values selected from the group consisting of the values in Table 2 in cm−1±2 cm−1; (b) one, two, three, four, five, or more than five wavenumber (cm−1) values selected from the group consisting of the characteristic values in Table 2 in cm−1±2 cm−1; or (c) wavenumber (cm−1) values essentially the same as shown in FIG. 2;
  III) a $^{13}$C solid state NMR spectrum (ppm) comprising: (a) one, two, three, four, five, or more than five resonance (ppm) values selected from the group consisting of the values in Table 3 in ppm±0.2 ppm; (b) one, two, three, four, five, or more than five resonance (ppm) values selected from the group consisting of the characteristic values in Table 3 in ppm±0.2 ppm; or (c) resonance (ppm) values essentially the same as shown in FIG. 3;
  IV) a solid state $^{19}$F spectrum (ppm) comprising: (a) one, two, or three resonance (ppm) values selected from the group consisting of the values in Table 4 in ppm±0.2 ppm; (b) the characteristic value in Table 3 in ppm±0.2 ppm; or (c) resonance (ppm) values essentially the same as shown in FIG. 3; and,
  V) a combination of any two, three or four of the foregoing embodiments (I)(a)-(c), (II)(a)-(c), (III)(a)-(c), or (IV)(a)-(c), provided they are not inconsistent with each other.

In another aspect, the present invention provides a crystalline form, according to any of the embodiments described herein, crystallized from a solvent system that may include acetone, methyl isobutyl ketone, 2-propanol, methanol, ethanol, water, or tetrahydrofuran.

In another aspect, the present invention also provides a pharmaceutical composition comprising crystalline ((S)-2,2-difluorocyclopropyl)-((1R,5S)-3-(2-((1-methyl-1H-pyrazol-4-yl)amino)pyrimidin-4-yl)-3,8-diazabicyclo[3.2.1]octan-8-yl)methanone and a pharmaceutically acceptable carrier.

In another aspect, the present invention also provides a method of treating a disease in a mammal, comprising administering to a mammal in need thereof a therapeutically effective amount of crystalline ((S)-2,2-difluorocyclopropyl)((1R,5S)-3-(2-((1-methyl-1H-pyrazol-4-yl)amino)pyrimidin-4-yl)-3,8-diazabicyclo-[3.2.1]octan-8-yl)-methanone or a pharmaceutically acceptable salt thereof or a pharmaceutical composition according to any of the embodiments described herein, said disease being selected from rheumatoid arthritis, lupus, psoriasis, psoriatic arthritis, atopic dermatitis, and inflammatory bowel disease.

DETAILED DESCRIPTION OF THE INVENTION

The present invention is directed to a crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone. The present invention is also directed to pharmaceutical compositions comprising the crystalline form, and to methods for preparing such forms. The invention is further directed to the use of the crystalline form in the treatment of various diseases.

There are a number of analytical methods one of ordinary skill in the art in solid-state chemistry can use to analyze solid forms. The term "analyze" as used herein means to obtain information about the solid-state structure of solid forms. For example, powder X-ray diffraction is a suitable technique for differentiating amorphous solid forms from crystalline solid forms and for characterizing and identifying crystalline solid forms of a compound. Powder X-ray diffraction is also suitable for quantifying the amount of a crystalline solid form (or forms) in a mixture. In X-ray powder diffraction, X-rays are directed onto a crystalline powder and the intensity of the diffracted X-rays is measured as a function of the angle between the X-ray source and the beam diffracted by the sample. The intensity of these diffracted X-rays can be plotted on a graph as peaks with the x-axis being the angle (this is known as the "2θ" angle) between the X-ray source and the diffracted X-rays and with the y-axis being the intensity of the diffracted X-rays. This graph is called a powder X-ray diffraction pattern or powder pattern. Different crystalline solid forms exhibit different powder patterns because the location of the peaks on the x-axis is a property of the solid-state structure of the crystal.

Such powder patterns, or portions thereof, can be used as an identifying fingerprint for a crystalline solid form. Thus, one could take a powder pattern of an unknown sample and compare that powder pattern with a reference powder pattern. A positive match would mean that the unknown sample is of the same crystalline solid form as that of the reference. One could also analyze an unknown sample containing a mixture of solid forms by adding and subtracting powder patterns of known compounds.

When selecting peaks in a powder pattern to characterize a crystalline solid form or when using a reference powder pattern to identify a form, one identifies a peak or collection of peaks in one form that are not present in the other solid forms.

The term "characterize" as used herein means to select an appropriate set of data capable of distinguishing one solid form from another. That set of data in powder X-ray diffraction is the position of one or more peaks. Selecting which powder X-ray diffraction peaks define a particular form is said to characterize that form.

The term "identify" as used herein means taking a selection of characteristic data for a solid form and using those data to determine whether that form is present in a sample. In powder X-ray diffraction, those data are the x-axis positions of the one or more peaks characterizing the form in question as discussed above. For example, once one determines that a select number of X-ray diffraction peaks characterize a particular solid form, one can use those peaks to determine whether that form is present in a sample.

When characterizing and/or identifying crystalline solid forms of the same chemical compound with powder X-ray diffraction, it is often not necessary to use the entire powder pattern. A smaller subset of the entire powder pattern can often be used to perform the characterization and/or identification. By selecting a collection of peaks that differentiate the crystalline solid form from other crystalline solid forms of the compound, one can rely on those peaks to both characterize the form and to identify the form in, for example, an unknown mixture. Additional data can be added, such as from another analytical technique or additional peaks from the powder pattern, to characterize and/or identify the form should, for instance, additional polymorphs be identified later.

Due to differences in instruments, samples, and sample preparation, peak values are sometimes reported with the modifier "about" in front of the peak values. This is common practice in the solid-state chemical arts because of the variation inherent in peak values. A typical precision of the 2θ x-axis value of a peak in a powder pattern is on the order of plus or minus 0.2° 2θ. Thus, a diffraction peak that appears at "about 9.2° 2θ," means that the peak could be between 9.0° 2θ and 9.4° 2θ when measured on most X-ray diffractometers under most conditions. Variability in peak intensity is a result of how individual crystals are oriented in the sample container with respect to the external X-ray source (known as "preferred orientation"). This orientation effect does not provide structural information about the crystal. Powder X-ray diffraction is just one of several analytical techniques one may use to characterize and/or identify crystalline solid forms. Spectroscopic techniques such as Raman (including microscopic Raman), infrared, and solid state NMR spectroscopies may be used to characterize and/or identify crystalline solid forms. These techniques may also be used to quantify the amount of one or more crystalline solid forms in a mixture and peak values can also be reported with the modifier "about" in front of the peak values. A typical variability for a peak value associated with an FT-Raman and FT-Infrared measurement is on the order of plus or minus 2 cm$^{-1}$. A typical variability for a peak value associated with a $^{13}$C or $^{19}$F chemical shift is on the order of plus or minus 0.2 ppm for crystalline material. A typical variability for a value associated with a differential scanning calorimetry onset temperature is on the order of plus or minus 5° C.

The term "room temperature" as used herein refers to the temperature range of 20° C. to 23° C.

In the first aspect, the present invention comprises a crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone having one or more characteristics selected from the group consisting of:

I) a powder X-ray diffraction pattern containing the following 2θ values measured using Cu K$_{α1}$ radiation (λ=1.54056 Å): 2θ, at 5.0, 9.9, and 15.3° 2θ±0.2° 2θ.

II) a powder X-ray diffraction pattern containing the following 2θ values measured using Cu K$_{α1}$ radiation (λ=1.54056 Å): 5.0, 9.9, 15.3, and 19.7° 2θ±0.2° 2θ.

III) a powder X-ray diffraction pattern containing the following 2θ values measured using Cu K$_{α1}$ radiation (λ=1.54056 Å): 5.0, 9.9, 15.3, 16.8 and 19.7° 2θ±0.2° 2θ.

Accordingly, the invention provides a crystalline form of ((S)-2,2-difluorocyclopropyl)-((1R,5S)-3-(2-((1-methyl-1H-pyrazol-4-yl)amino)-pyrimidin-4-yl)-3,8-diazabicyclo[3.2.1]octan-8-yl)methanone, having a powder X-ray diffraction pattern comprising peaks, in terms of 2θ, at 5.0, 9.9, and 15.3° 2θ±0.2° 2θ. The invention also provides a crystalline form of ((S)-2,2-difluorocyclopropyl)((1R,5S)-3-(2-((1-methyl-1H-pyrazol-4-yl)amino)-pyrimidin-4-yl)-3,8-diazabicyclo[3.2.1]octan-8-yl)methanone, having a powder X-ray diffraction pattern comprising peaks, at 5.0, 9.9, 15.3, and 19.7° 2θ±0.2° 2θ. The invention further provides a crystalline form of ((S)-2,2-difluorocyclopropyl)-((1R,5S)-3-(2-((1-methyl-1H-pyrazol-4-yl)amino)pyrimidin-4-yl)-3,8-diazabicyclo[3.2.1]-octan-8-yl)methanone, having a powder X-ray diffraction pattern comprising peaks at 5.0, 9.9, 15.3, 16.8 and 19.7° 2θ±0.2° 2θ. In addition, the invention provides a pharmaceutical composition comprising a crystalline form of ((S)-2,2-difluorocyclopropyl)((1R,5S)-3-(2-((1-methyl-1H-pyrazol-4-yl)amino)pyrimidin-4-yl)-3,8-diazabicyclo-[3.2.1]octan-8-yl)-methanone; and, a pharmaceutically acceptable carrier. In certain embodiments, the invention provides said pharmaceutical composition, wherein said crystalline form has a powder X-ray diffraction pattern comprising peaks at 5.0, 9.9, and 15.3° 2θ±0.2° 2θ. In other embodiments, the invention provides said pharmaceutical composition, wherein said crystalline form has a powder X-ray diffraction pattern comprising peaks at 5.0, 9.9, 15.3, and 19.7° 2θ±0.2° 2θ. In yet other embodiments, the invention provides said pharmaceutical composition, wherein said crystalline form has a powder X-ray diffraction pattern comprising peaks at 5.0, 9.9, 15.3, 16.8 and 19.7° 2θ±0.2° 2θ.

The invention also provides a pharmaceutical composition of said crystalline form, according to any of the embodiments described herein, comprising a topical formulation selected from a cream, transdermal patch, ointment, ophthalmic drops, lotion and gel. In certain embodiments, the invention provides said pharmaceutical composition wherein the topical formulation contains from about 0.1% to about 5.0% (w/v) crystalline ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone.

In addition, the invention provides a method of treating a disease in a mammal, comprising administering to a mammal in need thereof a therapeutically effective amount of a crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone, or a pharmaceutically acceptable salt thereof, and a pharmaceutically acceptable carrier, wherein the disease is selected from the group consisting of lupus, rheumatoid arthritis, IBD, ulcerative colitis, Crohn's Disease, vitiligo, alopecia, psoriasis and atopic dermatitis. In certain embodiments, the invention provides said method, wherein said crystalline form has a powder X-ray diffraction pattern comprising peaks at 5.0, 9.9, and 15.3° 2θ±0.2° 2θ. In certain other embodiments, the invention provides said crystalline form has a powder X-ray diffraction pattern comprising peaks at 5.0, 9.9, 15.3, and 19.7° 2θ±0.2° 2θ. In yet other certain embodiments, the invention provides said crystalline form has a powder X-ray diffraction pattern comprising peaks, in terms of 5.0, 9.9, 15.3, 16.8 and 19.7° 2θ±0.2° 2θ.

The invention also provides a method of topically treating a disease in a mammal, comprising administering by a topical mode of administration to a mammal in need thereof a therapeutically effective amount of a crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone, or a pharmaceutically acceptable salt thereof, and a pharmaceutically acceptable carrier, wherein the disease is selected from the group consisting of vitiligo, alopecia, psoriasis and atopic dermatitis. In certain embodiments, the invention provides said method, wherein said crystalline form has a powder X-ray diffraction pattern comprising peaks at 5.0, 9.9, and 15.3° 2θ±0.2° 2θ. In certain other embodiments, the invention provides said method, wherein said crystalline form has a powder X-ray diffraction pattern comprising peaks at 5.0, 9.9, 15.3, and 19.7° 2θ±0.2° 2θ. In certain other embodiments, the invention provides said method, wherein said crystalline form has a powder X-ray diffraction pattern comprising peaks 5.0, 9.9, 15.3, 16.8 and 19.7° 2θ±0.2° 2θ.

Instrument and Analysis Methods:

Calculated Powder Patterns: Powder patterns were calculated from single crystal X-ray data using the SHELXTL package of programs, including XFOG (SHELXTL, Bruker AXS, XFOG, Version 5.100, 1997) and XPOW (SHELXTL, Bruker AXS, XPOW, Version 5.102, 1997-2000). The appropriate wavelength needed for overlay graphics was added using the XCH file exchange program (SHELXTL, Bruker AXS, XCH, Version 5.0.4, 1995-2001).

Powder X-Ray Diffraction:

Powder X-ray diffraction analysis was conducted using a Bruker AXS D8 Advance diffractometer equipped with a Cu radiation source, equipped with a twin primary utilizing a gobel mirror. Diffracted radiation was detected by a LYNXEYE_EX detector with motorized slits. Both primary and secondary equipped with 2.5 soller slits. The X-ray tube voltage and amperage were set at 40 kV and 40 mA respectively. Data was collected in the Theta-Theta goniometer in a locked couple scan at Cu K-alpha wavelength from 3.0 to 40.0 degrees 2-Theta with 1204 steps using a scan speed of 0.50 seconds per step. Samples were prepared by placement in a silicon low background sample holder and rotated during collection. Data were collected using Bruker DIFFRAC Plus software. Analysis performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked and peak positions were adjusted to the peak maximum. Peaks with relative intensity of ≥2% were generally chosen. The peaks which were not resolved or were consistent with noise were not selected. A typical error associated with the peak position from PXRD is up to ±0.2° 2-Theta (USP-941).

PXRD Reflection Assignments: Eva Application 9.0 software was used to visualize and evaluate PXRD spectra. Peak values were assigned at the maximum intensity of a given reflection. All reflections exhibiting a relative intensity of greater than 10% are included within the following tables.

Solid State NMR: Solid state NMR (ssNMR) analysis was conducted on a CPMAS probe positioned into a Bruker-BioSpin Avance III™ 500 MHz ($^1$H frequency) NMR spectrometer. Material was packed into a 4 mm rotor sealed with a standard drive cap. A magic angle spinning rate of 15.0 kHz was used. A phase modulated proton decoupling field of 80-90 kHz was applied during spectral acquisition. $^{13}$C ssNMR spectrum was collected using a proton decoupled cross-polarization magic angle spinning (CPMAS) experiment. The cross-polarization contact time was set to 3 ms and the recycle delay to 60 seconds. The number of scans was adjusted to obtain an adequate signal to noise ratio, with 768 scans being collected for the API and more scans, typically ≥4096, being collected for a drug product. The $^{13}$C chemical shift scale was referenced using a $^{13}$C CPMAS experiment on an external standard of crystalline adamantane, setting its up-field resonance to 29.5 ppm.

$^{19}$F ssNMR spectrum was collected using a proton decoupled magic angle spinning (MAS) experiment. The recycle delay was set to 60 seconds. The number of scans was adjusted to obtain an adequate signal to noise ratio, with 64 scans being collected for the API and more scans, typically ≥256, being collected for a drug product. The $^{19}$F chemical shift scale was referenced using a proton decoupled $^{19}$F MAS experiment on an external standard 50/50 (volume/volume) of trifluoroacetic acid and water, setting its resonance to −76.54 ppm.

Automatic peak picking was performed using Bruker-BioSpin TopSpin™ version 3.5 software. Generally, a threshold value of 5% relative intensity was used for preliminary peak selection. The output of the automated peak picking was visually checked to ensure validity and adjustments were manually made if necessary. Although specific solid state NMR peak values are reported herein there does exist a range for these peak values due to differences in instruments, samples, and sample preparation. The solid state NMR peak heights reported herein are relative intensities. Solid state NMR intensities can vary depending on the actual setup of the CPMAS experimental parameters and the thermal history of the sample.

The present invention provides a crystalline form of ((S)-2,2-difluorocyclopropyl)-((1R,5S)-3-(2-((1-methyl-1H-pyrazol-4-yl)amino)pyrimidin-4-yl)-3,8-diazabicyclo[3.2.1]-octan-8-yl)methanone which can be identified by one or more solid state analytical methods. PXRD peak list for the crystalline form at 23° C. is shown in Table 1.

TABLE 1

PXRD peak list for ((S)-2,2-difluorocyclopropyl)-((1R,5S)-3-(2-((1-methyl-1H-pyrazol-4-yl)amino)pyrimidin-4-yl)-3,8-diazabicyclo[3.2.1]octan-8-yl)methanone, Form 1, prepared from Example 4. Asterisked peaks are characteristic for Form 1, anhydrous free base.

| Angle (2 Θ) | Relative Intensity (%) |
| --- | --- |
| 5.0* | 47.8 |
| 9.4 | 30.3 |
| 9.9* | 29.1 |
| 12.1 | 6.4 |
| 12.7 | 9.7 |
| 14.8 | 26.4 |
| 15.3* | 13 |
| 16.0 | 10.7 |
| 16.8* | 77.8 |
| 18.3 | 14.7 |
| 18.7 | 68.2 |
| 19.0 | 100 |
| 19.3 | 30 |
| 19.7* | 18.5 |
| 20.3 | 12.5 |
| 20.7 | 65.8 |
| 20.8 | 65.1 |
| 21.3 | 4.6 |
| 22.8 | 20.4 |
| 23.4 | 21.8 |
| 23.7 | 15.4 |
| 24.2 | 12.5 |
| 24.7 | 18 |
| 27.5 | 16.7 |
| 27.9 | 5.2 |
| 28.2 | 3.8 |
| 29.8 | 4 |

Intensities can vary depending on the actual setup of the CPMAS experimental parameters and the thermal history of the sample. CPMAS intensities are not necessarily quantitative.

Raman spectral peaks for the crystalline form are shown in Table 2.

TABLE 2

Full Raman peak list for ((S)-2,2-difluorocyclopropyl)-((1R,5S)-3-(2-((1-methyl-1H-pyrazol-4-yl)amino)pyrimidin-4-yl)-3,8-diazabicyclo[3.2.1]octan-8-yl)methanone, Form 1. Asterisked peaks are characteristic for Form 1 (S = strong, M = medium, W = weak).

| Raman peak position (cm−1) | Normalized intensity |
| --- | --- |
| 111 | S |
| 145 | M |
| 165 | M |
| 178 | M |
| 203 | W |
| 244 | W |
| 280 | W |
| 304 | W |
| 336 | W |
| 356 | W |
| 367 | W |
| 384 | W |
| 413 | W |
| 459 | W |
| 486 | W |

TABLE 2-continued

Full Raman peak list for ((S)-2,2-difluorocyclopropyl)-((1R,5S)-3-(2-((1-methyl-1H-pyrazol-4-yl)amino)pyrimidin-4-yl)-3,8-diazabicyclo[3.2.1]octan-8-yl)methanone, Form 1. Asterisked peaks are characteristic for Form 1 (S = strong, M = medium, W = weak).

| Raman peak position (cm−1) | Normalized intensity |
| --- | --- |
| 513 | W |
| 543 | W |
| 588 | W |
| 616 | W |
| 642 | W |
| 649 | W |
| 681 | W |
| 714 | W |
| 735 | W |
| 768 | W |
| 780 | W |
| 792 | W |
| 814 | W |
| 836 | W |
| 847 | W |
| 868 | W |
| 886 | M |
| 906 | W |
| 915 | W |
| 950 | W |
| 975* | S |
| 987 | M |
| 1011 | W |
| 1022 | M |
| 1032 | W |
| 1054 | W |
| 1077 | W |
| 1091 | W |
| 1115* | M |
| 1152 | W |
| 1169 | W |
| 1198 | W |
| 1220 | W |
| 1243 | W |
| 1259 | W |
| 1280 | W |
| 1297 | W |
| 1322 | W |
| 1346 | M |
| 1358 | M |
| 1366 | M |
| 1375 | M |
| 1387 | M |
| 1415 | W |
| 1443 | W |
| 1455 | W |
| 1481 | W |
| 1538 | W |
| 1566* | M |
| 1578* | M |
| 1605* | M |
| 1638 | W |
| 1944 | W |
| 1022 | M |
| 1032 | W |
| 1054 | W |
| 1077 | W |
| 1091 | W |
| 1115* | M |
| 1152 | W |
| 1169 | W |
| 1198 | W |
| 1220 | W |
| 1243 | W |
| 1259 | W |
| 1280 | W |
| 1297 | W |
| 1322 | W |
| 1346 | M |
| 1358 | M |
| 1366 | M |

TABLE 2-continued

Full Raman peak list for ((S)-2,2-difluorocyclopropyl)-
((1R,5S)-3-(2-((1-methyl-1H-pyrazol-4-yl)amino)pyrimidin-
4-yl)-3,8-diazabicyclo[3.2.1]octan-8-yl)methanone,
Form 1. Asterisked peaks are characteristic for Form
1 (S = strong, M = medium, W = weak).

| Raman peak position (cm−1) | Normalized intensity |
|---|---|
| 1375 | M |
| 1387 | M |
| 1415 | W |
| 1443 | W |
| 1455 | W |
| 1481 | W |
| 1538 | W |
| 1566* | M |
| 1578* | M |
| 1605* | M |
| 1638 | W |
| 1944 | W |
| 2487 | W |
| 2705 | W |
| 2746 | W |
| 2857 | W |
| 2872 | W |
| 2897 | W |
| 2956 | M |
| 2969 | M |
| 2987 | M |
| 3021 | S |
| 3095 | M |
| 3107 | W |
| 3187 | W |
| 3238 | W |

Figure 4:
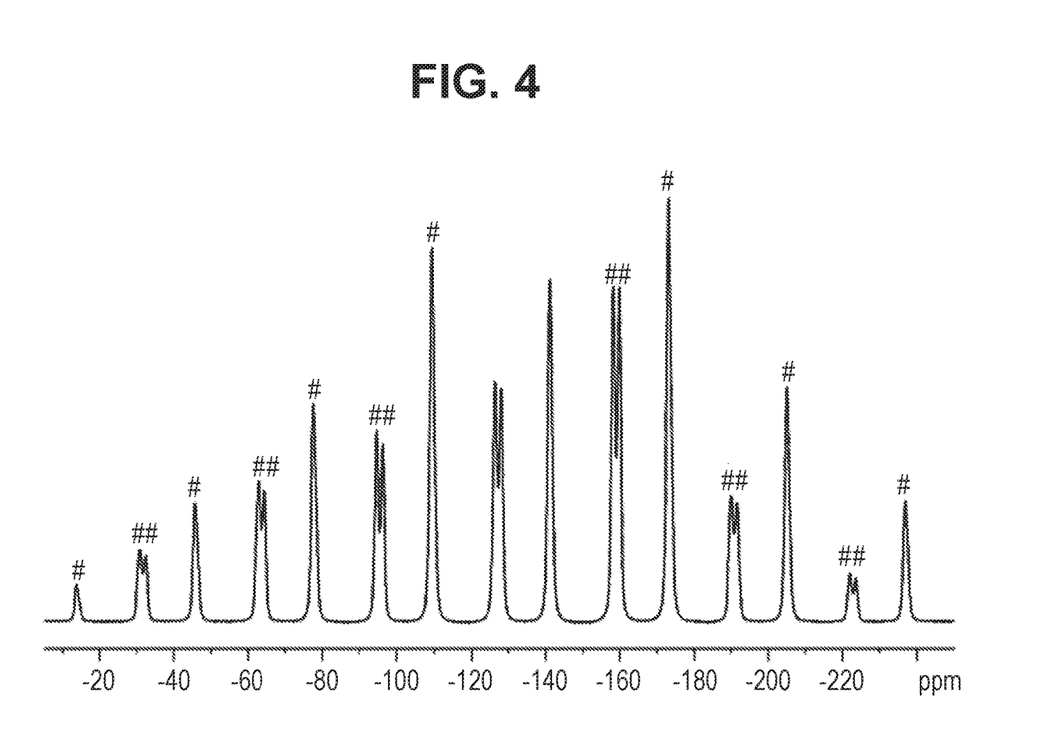
FIG. 4 depicts a solid state $^{19}$F nuclear magnetic resonance spectrum of crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone. Spinning side-bands are noted with hash marks.

$^{13}$C solid state and $^{19}$F solid state NMR peak lists for the crystalline form are shown respectively in Tables 3 and 4.

TABLE 3

$^{13}$C solid state NMR peak list for ((S)-2,2-difluorocyclopropyl)-
((1R,5S)-3-(2-((1-methyl-1H-pyrazol-4-yl)amino)pyrimidin-
4-yl)-3,8-diazabicyclo[3.2.1]octan-8-yl)methanone, Form
1. Asterisked peaks are characteristic for Form 1.

| $^{13}$C Chemical Shifts (ppm) | Relative Intensity % |
|---|---|
| 13.4 | 25 |
| 16.3 | 28 |
| 24.5 | 35 |
| 26.7 | 43 |
| 27.5 | 63 |
| 28.0 | 92 |
| 38.6* | 85 |
| 49.4 | 36 |
| 50.4 | 51 |
| 51.0 | 100 |
| 51.5 | 87 |
| 54.6* | 84 |
| 93.3 | 55 |
| 93.4 | 55 |
| 110.4 | 8 |
| 114.0 | 9 |
| 123.5 | 66 |
| 124.9* | 67 |
| 129.8* | 60 |
| 156.2 | 51 |
| 159.6 | 77 |
| 160.8 | 32 |
| 165.3* | 54 |

TABLE 4

$^{19}$F solid state NMR peak list for ((S)-2,2-difluorocyclopropyl)-
((1R,5S)-3-(2-((1-methyl-1H-pyrazol-4-yl)-amino)-pyrimidin-
4-yl)-3,8-diazabicyclo[3.2.1]octan-8-yl)methanone, Form
1. Asterisked peaks are characteristic for Form 1.

| $^{19}$F Chemical shift (ppm) | Relative intensity % |
|---|---|
| −141.2* | 100 |
| −128.1 | 68 |
| −126.5 | 70. |

Accordingly, the present invention provides pharmaceutical compositions comprising a crystalline form, and to methods for preparing such forms, as well as pharmaceutical compositions for use in medicine and for use in treating such diseases as lupus, rheumatoid arthritis, IBD, ulcerative colitis, Crohn's Disease, vitiligo, alopecia, psoriasis, psoriatic arthritis, and atopic dermatitis. The present invention also provides the use of such pharmaceutical compositions in the manufacture of a medicament for treating such diseases as lupus, rheumatoid arthritis, IBD, ulcerative colitis, Crohn's Disease, vitiligo, alopecia, psoriasis and atopic dermatitis.

The present invention further provides a crystalline form of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)-methanone, prepared by re-crystallizing ((2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone) from a suitable solvent.

The present invention also provides a topical formulation of ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)-methanone, prepared by combining a crystalline form thereof with excipients suitable for transdermal administration.

Methods of treating the diseases and syndromes listed herein are understood to involve administering to an individual in need of such treatment a therapeutically effective amount of the polymorph of the invention, or a composition containing the same. As used herein, the term "treating" in reference to a disease is meant to refer to preventing, inhibiting and/or ameliorating the disease.

As used herein, the term "individual" or "patient," used interchangeably, refers to any animal, including mammals, preferably mice, rats, other rodents, rabbits, dogs, cats, swine, cattle, sheep, goats, horses, or primates, and most preferably humans. As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

Dosage and Formulation

The invention also includes pharmaceutical compositions utilizing one or more of the present crystalline forms along with one or more pharmaceutically acceptable carriers, excipients, vehicles, etc.

The crystalline form of the invention is administered in an amount effective to treat a condition as described herein, and can be administered as crystalline compound per se, or alternatively, as a pharmaceutically acceptable salt. For administration and dosing purposes, the crystalline compound per se or pharmaceutically acceptable salt thereof will simply be referred to as the compounds of the invention.

The compounds of the invention are administered by any suitable route in the form of a pharmaceutical composition adapted to such a route, and in a dose effective for the treatment intended. The compounds of the invention may be administered orally, rectally, vaginally, parenterally, or topically.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds of the invention and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the invention is typically from about 0.01 to about 100 mg/kg (i.e., mg compound of the invention per kg body weight) for the treatment of the indicated conditions discussed herein. In another embodiment, total daily dose of the compound of the invention is from about 0.1 to about 50 mg/kg, and in another embodiment, from about 0.5 to about 30 mg/kg.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the invention include mammalian subjects. Mammals according to the invention include canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises pharmaceutical compositions. Such pharmaceutical compositions comprise a compound of the invention presented with a pharmaceutically acceptable carrier. Other pharmacologically active substances can also be present. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dose form is sub-lingual, such as, for example, a lozenge. In such solid dosage forms, the crystalline compound is ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a crystalline compound which enhances absorption or penetration of the active ingredient through the skin or other affected areas. When the crystalline compound of this invention is administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Accordingly, topical formulations of the presently disclosed crystalline form of ((S)-2,2-difluorocyclopropyl) ((1R,5S)-3-(2-((1-methyl-1H-pyrazol-4-yl)amino)pyrimidin-4-yl)-3,8-diazabicyclo[3.2.1]octan-8-yl)methanone may be administered using such preparations encompassing all conventional methods of administration across the surface of the body and the inner linings of body passages including epithelial and mucosal tissues, including transdermal, epidermal, buccal, pulmonary, ophthalmic, intranasal, vaginal and rectal modes of administration. Typical carriers include alcohol, water, mineral oil, liquid petrolatum, white petrolatum, glycerin, polyethylene glycol and propylene glycol. Such topical formulations may be prepared in combination with additional pharmaceutically acceptable excipients. An excipient which may be essential to clinical efficacy is one or more penetration enhancer such as be one or more saturated or cis-unsaturated C10-C18 fatty alcohols. Such fatty alcohols include C16-C18 fatty alcohols, and most preferably, are a C18 fatty alcohol. Examples of cis-unsaturated C16-C18 fatty alcohols include oleyl alcohol, linoleyl alcohol, γ-linolenyl alcohol and linolenyl alcohol. Saturated C10-C18 fatty alcohols useful as penetration enhancers include decyl alcohol, lauryl alcohol, myristyl alcohol, cetyl alcohol and stearyl alcohol. Alternatively, other penetration enhancers which may be used to prepare the topical formulations include C10-C18 fatty acids, which when saturated may include capric acid, lauric acid, myristic acid, palmitic acid, stearic acid and arachidic acid. Alternatively, the penetration enhancer may usefully be a cis-unsaturated fatty acid, such as palmitoleic acid (cis-9-hexadecenoic acid), oleic acid (cis-9-octadecenoic acid), cis-vaccenic acid (cis-11-octadecenoic acid), linoleic acid (cis-9,12-octadecadienoic acid), γ-linolenic acid (cis-6,9,12-octadecatrienoic acid), linolenic acid (cis-9,12,15-octadecatrienoic acid) and arachidonic acid (cis-5,8,11,14-eicosatetraenoic acid). The penetration enhancers, for example, one selected from C10-C18 fatty alcohols, are used in amounts ranging from about 0.1 to about 5% (w/v), more preferably, from 1 to about 4%, more preferably still, 1 to about 3% (w/v).

Topical formulations contain ((S)-2,2-difluorocyclopropyl)-((1R,5S)-3-(2-((1-methyl-1H-pyrazol-4-yl)amino)pyrimidin-4-yl)-3,8-diazabicyclo[3.2.1]octan-8-yl)methanone in therapeutically effective amounts that can be given in daily or twice daily doses to patients in need. These amounts range from about 0.1% to about 5.0% (w/v), more preferably, from about 0.1% to about 3.0% (w/v). Among other excipients which enhance the stability of these formulations include aldehyde scavengers, such as glycerine and propylene glycol, and antioxidants, such as butyl hydroxyanisole (BHA), butyl hydroxytoluene (BHT), propyl gallate, ascorbic acid (Vitamin C), polyphenols, tocopherols (Vitamin E), and their derivatives.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the crystalline compound of the invention is conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pennsylvania, 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

The crystalline compound of the invention can be used alone, or in combination with other therapeutic agents. The invention provides any of the uses, methods or compositions as defined herein wherein the crystalline compound herein, or pharmaceutically acceptable solvate of said compound, is used in combination with one or more other therapeutic agent discussed herein.

The administration of two or more compounds "in combination" means that all of the compounds are administered closely enough in time that the presence of one alters the biological effects of any other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the invention provides methods of treatment that include administering the crystalline compound of the invention in combination with one or more other pharmaceutical agents, wherein the one or more other pharmaceutical agents may be selected from the agents discussed herein.

These agents and the crystalline compound of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the antibody/compound of the invention, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for intravenous administration must be sterile. This is readily accomplished by, for example, filtration through sterile filtration membranes. Crystalline compound of the invention is generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The compounds of these teachings can be prepared by methods known in the art. The reagents used in the preparation of the compounds of these teachings can be either commercially obtained or can be prepared by standard procedures described in the literature. For example, compounds of the present invention can be prepared according to the methods illustrated in the following examples.

The description of this invention utilizes a variety of abbreviations well known to those skilled in the art, including the following:

aq.: aqueous
$CH_3CN$: Acetonitrile
DCM: Dichloromethane
DMF: N,N-Dimethylformamide
DMSO: Dimethylsulfoxide
EtOAc: Ethyl acetate
EtOH: Ethanol
FT-IR: Fourier Transform-Infrared
HOAc: Acetic acid
MeOH: Methanol PXRD: powder X-ray diffraction
ss $^{13}$C NMR: solid state $^{13}$C nuclear magnetic resonance
THF: Tetrahydrofuran
TLC: Thin Layer Chromatography

EXAMPLES

The following non-limiting example is presented merely to illustrate the present invention. The skilled person will understand that there are numerous equivalents and variations not exemplified but which still form part of the present teachings.

Example 1

Preparation of ((S)-2,2-difluorocyclopropyl)-((1R, 5S)-3-(2-((1-methyl-1H-pyrazol-4-yl)amino)-pyrimidin-4-yl)-3,8-diazabicyclo[3.2.1]octan-8-yl)methanone The Title compound was prepared according to Example 2 of U.S. Pat. No. 9,035,074. The crude material is warmed in 10 vol (100 mg/ml) 2:1 EtOH/water to 80° C. (until entirely dissolved), and then filtered, and slowly cooled until the product crystallizes. After filtration, the material is dried under vacuum at 45-55° C.

Example 2

Preparation of ((S)-2,2-difluorocyclopropyl)((1R, 5S)-3-(2-((1-methyl-1H-pyrazol-4-yl)amino)pyrimidin-4-yl)-3,8-diazabicyclo[3.2.1]octan-8-yl)methanone Form I One Molar aqueous sodium hydroxide solution (1.2 equiv) and p-Toluenesulfonic acid salt of ((S)-2,2-difluorocyclopropyl)((1R,5S)-3-(2-((1-methyl-1H-pyrazol-4-yl)amino)-pyrimidin-4-yl)-3,8-diazabicyclo[3.2.1]octan-8-yl)methanone (1.0 equiv) were combined in methyl isobutyl ketone (MIBK) (8 mL/g). After the solids dissolve and the salt is neutralized, the two liquid layers are allowed to separate. The aqueous layer is back-extracted with MIBK (5 mL/g) and the combined organic layers are washed with water (3 mL/g). The washed organic solution is speck free filtered and concentrated to remove water. The concentrate is diluted with MIBK (total volume=6.8 mL/g with respect to free base ((S)-2,2-difluorocyclopropyl)((1R,5S)-3-(2-((1-methyl-1H-pyrazol-4-yl)amino)-pyrimidin-4-yl)-3,8-diazabicyclo[3.2.1]octan-8-yl)methanone), heated to 75° C., then further diluted with n-heptane (3.2 mL/g with respect to (S)-2,2-difluorocyclopropyl)-((1R,5S)-3-(2-((1-methyl-1H-pyrazol-4-yl)amino)-pyrimidin-4-yl)-3,8-diazabicyclo[3.2.1]-octan-8-yl)methanone to give an approximate 2:1 v/v MIBK:n-heptane solution of the free base. The solution is cooled slightly to 65° C. and seeded with 0.02 mol % free base ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone) Form 1 (0.02 equiv) while warm. The free base API is allowed to crystallize at 65 C for ~1 hour and the resulting slurry is cooled to ambient temperature (~20° C. at 0.1° C./min) and held at that temperature for 14 hours to complete the crystallization. Free base ((S)-2,2-difluorocyclopropyl)-((1R,5S)-3-(2-((1-methyl-1H-pyrazol-4-yl)amino)pyrimidin-4-yl)-3,8-diazabicyclo[3.2.1]octan-8-yl)-methanone) is collected by filtration, washed with 3:7 v/v MIBK/n-heptane (0.7 mL/g) and dried in the filter, or optionally in a vacuum oven at 45° C.

Example 3

Preparation of Free Base (S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone Amorphous free base ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone) (100 mg) and ethyl acetate (EtOAc) (1 mL) were added to a vial to form a solution, and heated to 60° C. Heptane was added until a precipitate appeared, then EtOAc was added back in until the precipitate dissolved again. The solution was cooled to room temperature (RT) and stirred at RT overnight. Clear oil droplets were on the bottom of vial, so the mixture was heated to 60° C. then allowed to cool at ambient conditions. Racemate crystal seed prepared in accordance with U.S. Pat. No. 9,035,074 was added, and the mixture was stirred at RT overnight. The mixture (seed from racemate was still undissolved, but no other precipitation had occurred) was heated at 35° C. for ~64 hrs. The resulting precipitate was filtered as crystalline free base ((S)-2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)-methanone) Form 1.

Example 4

Preparation of Racemate: ((2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone)

One and 0.72 mmol of racemate ((2,2-difluorocyclopropyl)((1R,5S)-3-(2-((1-methyl-1H-pyrazol-4-yl)amino)pyrimidin-4-yl)-3,8-diazabicyclo[3.2.1]octan-8-yl)methanone), 1 mol of (S)-2,2-difluorocyclopropane-1-carboxylic acid, 2.06 mol HATU (1-[Bis(dimethylamino)methylene]-1H-1,2,3-triazolo[4,5-b]pyridinium 3-oxido hexafluorophosphate, N-[(Dimethylamino)-1H-1,2,3-triazolo-[4,5-b]pyridin-1-ylmethylene]-N-methylmethanaminium hexafluorophosphate N-oxide) and 8 mL dichloromethane were added to a flask at RT, followed by addition of 6.88 mmol of DIEA (N,N-Diisopropylethylamine). The reaction was stirred at RT for 6 hrs. Solvent was removed and the resulting reaction crude material was purified using silica gel chromatography and eluted with 30% ethyl acetate 70% heptane to 100% ethyl acetate. It was further purified by silica gel chromatography with 8% methanol (MeOH) and 92% dichloromethane (DCM). The sample was dissolved in DCM and washed with water saturated with ammonium chloride (NH$_4$Cl) three times. The organic layer was concentrated to a gum. The residue was placed in a flask and 3 mL of EtOAc was added and heated to 60° C., then heptane was added until a precipitate appeared, then EtOAc was added back in until the precipitate dissolved again. The solution was cooled to RT and stirred overnight at RT. The resulting precipitate was temperature cycled twice with the following parameters: hold at 60° C. for 2 h then cool to 20° C. and hold for an additional 18 hrs. The solid was filtered and dried under vacuum. PXRD showed that this solid was crystalline.

Variations, modifications, and other implementations of what is described herein will occur to those skilled in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

Each of the printed publications, including but not limited to patents, patent applications, books, technical papers, trade publications and journal articles described or referenced in this specification are herein incorporated by reference in their entirety and for all purposes.

We claim:

1. A crystalline form of ((S)-2,2-difluorocyclopropyl) ((1R,5S)-3-(2-((1-methyl-1H-pyrazol-4-yl)amino) pyrimidin-4-yl)-3,8-diazabicyclo[3.2.1]octan-8-yl)methanone, or a pharmaceutically acceptable salt thereof, wherein the crystalline form is characterized by a powder X-ray diffraction pattern comprising peaks, in terms of 2θ, at 5.0, 9.9, and 15.3° 2θ±0.2°2θ.

2. The crystalline form of claim 1, further characterized by a powder X-ray diffraction pattern peak, in terms of 2θ, at 19.7° 2θ±0.2° 2θ.

3. The crystalline form of claim 1, further characterized by a powder X-ray diffraction pattern comprising peaks, in terms of 2θ, at 16.8 and 19.7° 2θ±0.2° 2θ.

4. The crystalline form of claim 1, where said form is non-hygroscopic and anhydrous.

5. The crystalline form of claim 1, characterized by at least one solid state 13C nuclear magnetic resonance chemical shift selected from the group consisting of 54.6, 129.8, and 124.9 ppm±0.2 ppm.

6. The crystalline form of claim 1, characterized by a set of Raman bands at 1578, 1605, and 1566 $cm^{-1}$±2 $cm^{-1}$.

7. The crystalline form of claim 1, further characterized by a Raman band at 1578 $cm^{-1}$±2 $cm^{-1}$.

8. The crystalline form of claim 1, further characterized by a Raman band at 1578 $cm^{-1}$±2 $cm^{-1}$ and at least one solid state 13C nuclear magnetic resonance chemical shift selected from the group consisting of 54.6 and 129 ppm±0.2 ppm.

9. A pharmaceutical composition comprising the crystalline form of claim 1 or a pharmaceutically acceptable salt thereof; and, a pharmaceutically acceptable carrier.

10. The pharmaceutical composition of claim 9, comprising a topical formulation selected from a cream, transdermal patch, ointment, ophthalmic drops, lotion and gel.

11. The pharmaceutical composition of claim 10 wherein the topical formulation contains about 0.1% to about 5.0% (w/v) crystalline ((S)-2,2-difluorocyclopropyl)-((1R,5S)-3-(2-((1-methyl-1H-pyrazol-4-yl)amino)-pyrimidin-4-yl)-3,8-diazabicyclo[3.2.1]octan-8-yl)methanone or a pharmaceutically acceptable salt thereof.

12. A method of treating a disease in a mammal, comprising administering to a mammal in need thereof a therapeutically effective amount of a crystalline form of claim 1 or a pharmaceutically acceptable salt thereof, wherein the disease is selected from the group consisting of lupus, rheumatoid arthritis, IBD, ulcerative colitis, Crohn's Disease, vitiligo, alopecia, psoriasis, psoriatic arthritis, and atopic dermatitis.

13. A method of topically treating a disease in a mammal, comprising administering by a topical mode of administration to a mammal in need thereof a therapeutically effective amount of a crystalline form of claim 1 or a pharmaceutically acceptable salt thereof wherein the disease is selected from the group consisting of vitiligo, alopecia, psoriasis and atopic dermatitis.

14. The crystalline form of claim 1 or a pharmaceutically acceptable salt thereof for use as a medicament.

15. The crystalline form of claim 1 or a pharmaceutically acceptable salt thereof for use in the treatment of a disorder selected from the group consisting of lupus, rheumatoid arthritis, IBD, ulcerative colitis, Crohn's Disease, vitiligo, alopecia, psoriasis, psoriatic arthritis, and atopic dermatitis.

16. A crystalline form of ((S)-2,2-difluorocyclopropyl) ((1R,5S)-3-(2-((1-methyl-1H-pyrazol-4-yl)amino) pyrimidin-4-yl)-3,8-diazabicyclo[3.2.1]octan-8-yl)-methanone, or a pharmaceutically acceptable salt thereof, prepared by re-crystallizing ((2,2-difluorocyclopropyl)-((1R,5S)-3-(2-((1-methyl-1H-pyrazol-4-yl)amino)-pyrimidin-4-yl)-3,8-diazabicyclo[3.2.1]octan-8-yl)methanone) from a suitable solvent, wherein the crystalline form is characterized by a powder X-ray diffraction pattern comprising peaks, in terms of 2θ, at 5.0, 9.9, and 15.3° 2θ±0.2° 2θ.

17. A topical formulation of comprising a crystalline form of ((S)-2,2-difluorocyclopropyl) ((1R,5S)-3-(2-((1-methyl-1H-pyrazol-4-yl)amino) pyrimidin-4-yl)-3,8-diazabicyclo[3.2.1]octan-8-yl)methanone, or a pharmaceutically acceptable salt thereof, prepared by combining the crystalline form or the pharmaceutically acceptable salt thereof with excipients suitable for transdermal administration, wherein the crystalline form is characterized by a powder X-ray diffraction pattern comprising peaks, in terms of 2θ, at 5.0, 9.9, and 15.3° 2θ±0.2° 2θ.

* * * * *